United States Patent [19]

Pizer

[11] 4,282,864
[45] Aug. 11, 1981

[54] METHOD AND APPARATUS FOR INDUCING A PRE-HYPNOTIC STATE

[76] Inventor: Robert S. Pizer, 4007 Connecticut Ave. N. W., Washington, D.C. 20008

[21] Appl. No.: 148,785

[22] Filed: May 12, 1980

[51] Int. Cl.³ .............................................. A61N 1/34
[52] U.S. Cl. .................................... 128/1 C; 128/905
[58] Field of Search ............... 128/1 C, 732, 687, 689, 128/905

[56] References Cited

U.S. PATENT DOCUMENTS

| 3,576,185 | 4/1971 | Schulz et al. | 128/1 C |
| 3,858,574 | 1/1975 | Page | 128/689 |
| 3,905,355 | 9/1975 | Brudny | 128/905 |
| 4,181,134 | 1/1980 | Mason et al. | 128/689 |

Primary Examiner—William E. Kamm
Attorney, Agent, or Firm—Laubscher & Laubscher

[57] ABSTRACT

A device for inducing a pre-hypnotic state of profound relaxation in an individual is disclosed wherein the individual's mind is receptive to suggestion. The device is characterized in that biofeedback signals from the individual are used to produce a plurality of pulsed physical stimuli having a frequency of twice that of the heartbeat rate of the individual. The device includes a heartbeat sensor for producing a first pulse signal, the pulses of which correspond with the heartbeat of the individual. An interpolation device is connected with the heartbeat sensor to produce a second pulse signal, the pulses of which occur midway in time between successive pairs of heartbeat pulses, respectively. The interpolation device includes a voltage ramp generator responsive to the first pulse signal to produce a linear voltage ramp output the peaks of which are in synchronization with the pulses of the first signal, respectively, the amplitude of the voltage peaks corresponding with the heartbeat rate of the individual. The interpolation device further includes a peak detector for sensing the peaks of the voltage ramp output and a comparator connected with the peak detector for sensing the midpoint of the voltage ramp output between successive peaks to produce the second pulse signal. A physical stimulus device having a pair of inputs connected with the heartbeat sensor and the interpolation device, respectively, produces a pulsed physical stimulus in response to the first and second signals and having a frequency of twice the heartbeat rate of the individual. Application of such a biofeedback pulsed physical stimulus induces a pre-hypnotic state of profound relaxation in the individual.

14 Claims, 5 Drawing Figures

METHOD AND APPARATUS FOR INDUCING A PRE-HYPNOTIC STATE

BRIEF DESCRIPTION OF THE PRIOR ART

Various hypnogogic and sleep-inducing devices are well-known in the patented prior art. Such devices have used the principles of spinning spirals, swinging pendulums, flashing lights, etc., to produce either a hypnotic or sleepy state in an individual. The patent to Hull U.S. Pat. No. 2,304,095, for example, discloses a method and apparatus for inducing and sustaining sleep by applying audible or tactual vibrations to an individual. Sound or tactual vibratory motion of a sustained pitch and amplitude is applied to the individual and provision is made for varying the pitch or amplitude of the applied vibrations to a rate somewhat slower than either the heartbeat of respiration rate of the individual. The Condict U.S. Pat. No. 3,495,596 teaches a method and apparatus for processing an individual's electroencephalograph signal by amplitude modulation and feeding the processed signal back to the individual to induce sleep. Similarly, the Monroe U.S. Pat. No. 3,884,218 discloses a method of inducing sleep in an individual wherein an audio signal is generated comprising a repetitive sound modulated by the individual's electroencephalogram.

While the prior devices normally operate quite satisfactorily with regard to inducing sleep, they each suffer from the inherent drawback of not being able to quickly and efficiently induce a pre-hypnotic state of profound relaxation in an individual.

BACKGROUND OF THE INVENTION

The present invention was developed to overcome the aforementioned disadvantages by providing a method and apparatus for inducing a pre-hypnotic relaxed state in various types of individuals while minimizing the discomfort to the individual.

More specifically, the present invention is a biofeedback device which makes use of the natural physiological phenomenon wherein application of a pulsed physical stimulus in synchronization with and having a frequency of twice the heartbeat rate of an individual induces a pre-hypnotic state of profound relaxation in the individual. As a consequence of this state of relaxation, the mind of the individual is receptive to suggestion. The aforementioned physiological phenomenon occurs only when the applied pulsed stimulus has a frequency of twice that of the individual and when the stimulus is applied in synchronization with the individual's heartbeat.

SUMMARY OF THE INVENTION

Accordingly, it is a primary object of the present invention to provide a biofeedback device for inducing a pre-hypnotic state in an individual wherein the individual's mind is receptive to suggestion. The device includes a heartbeat sensing device for sensing the heartbeat rate of the individual to produce a first pulse signal and an interpolation device responsive to the heartbeat sensing device to produce a second pulse signal midway in time between successive pairs of heartbeat pulses. The interpolation device includes a voltage ramp generator for producing a linear voltage ramp output the peaks of which are in synchronization with the pulses of the first signal from the heartbeat sensor, respectively. The amplitude of the peaks of the voltage ramp correspond with the heartbeat rate of the individual. The interpolation device further includes a peak detector for sensing the peaks of the voltage ramp output and a comparator device biased to sense the midpoint between successive peaks of the voltage ramp output to produce the second signal. A physical stimulus device receives the first pulse output from the heartbeat sensor device and the second pulse output from the interpolation device to produce a pulsed physical stimulus having a frequency which is twice the heartbeat rate of the individual. The pulsed physical stimulus when applied to the individual induces a pre-hypnotic state of profound relaxation, whereby the individual may readily be hypnotized or prepared for sleep.

According to a more specific object of the invention, the heartbeat sensor device comprises an electro-optic sensor which produces a signal corresponding with the heartbeat of the individual. The signal is amplified and modified to produce a first pulse signal having a fast pulse transition time.

According to a further object of the invention, the physical stimulus comprises a visual stimulus, an audio stimulus, or a combination of the two.

BRIEF DESCRIPTION OF THE DRAWING

Other objects and advantages of the invention will become apparent from a study of the following specification when viewed in the light of the accompanying drawing, in which.

DETAILED DESCRIPTION

Figure 1:
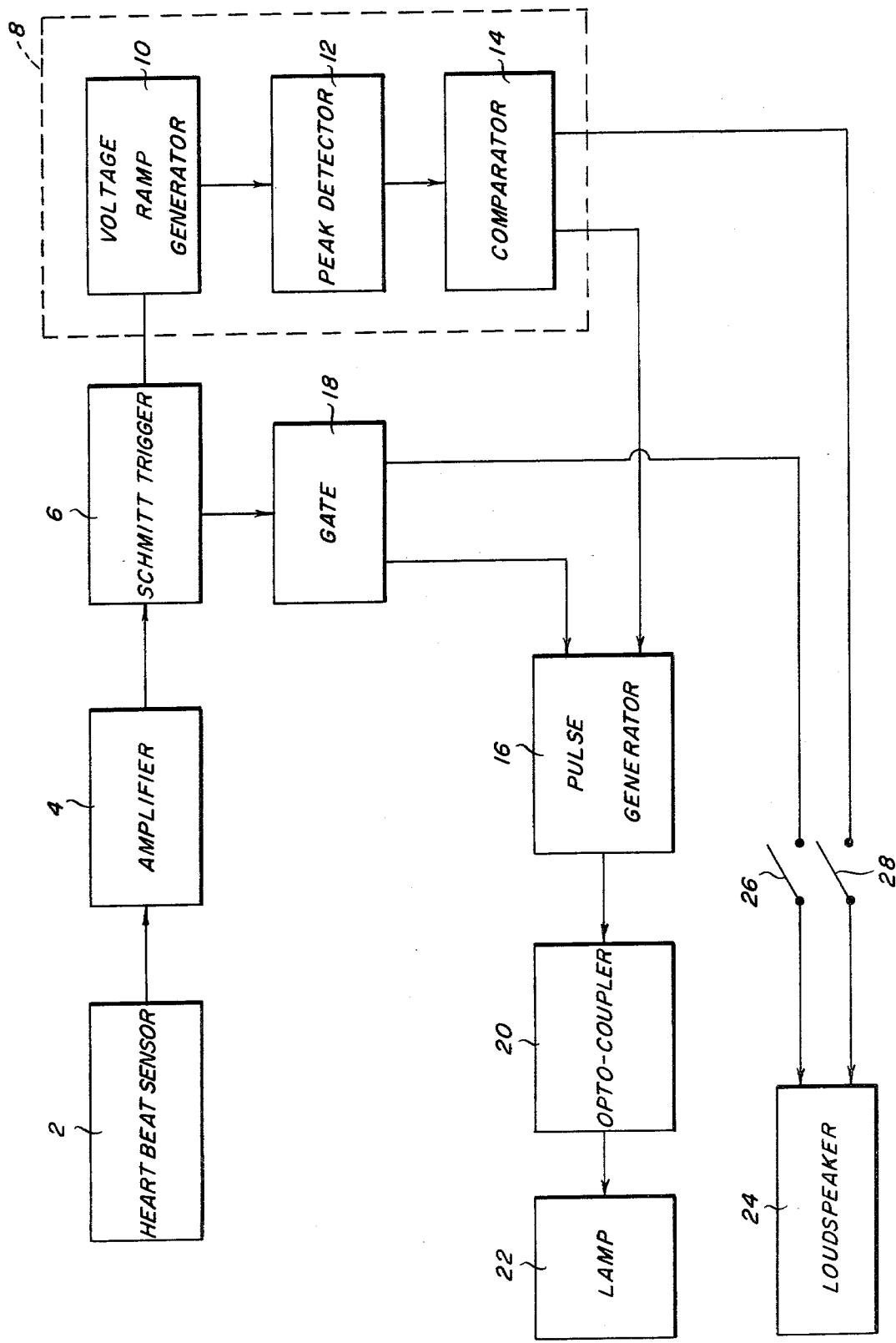
FIG. 1 is a block diagram of one form of the prehypnotic state inducing device.

Referring first more particularly to FIG. 1, the biofeedback device according to the present invention includes a heartbeat sensor 2 which senses the heartbeat of an individual and produces a first signal corresponding therewith. An amplifier 4 amplifies the first signal, and a regenerative comparator such as a Schmitt trigger 6 modifies the first signal to produce a signal having a fast pulse transition time. The modified first signal is supplied to an interpolation device 8 which produces a second pulse signal the pulses of which occur midway in time between successive pairs of the first heartbeat pulses, respectively. The interpolation device includes a voltage ramp generator 10 which receives the modified first pulse signal and generates a linear voltage ramp output the peaks of which are in synchronization with the pulses of the first signal, respectively. The amplitude of the voltage peaks corresponds with the heartbeat rate of the individual. A peak detector 12 senses the peaks of the voltage ramp output and a comparator device 14 connected with the peak detector senses the mid-point of the voltage ramp output between successive peaks and produces the second signal.

Figure 2A:
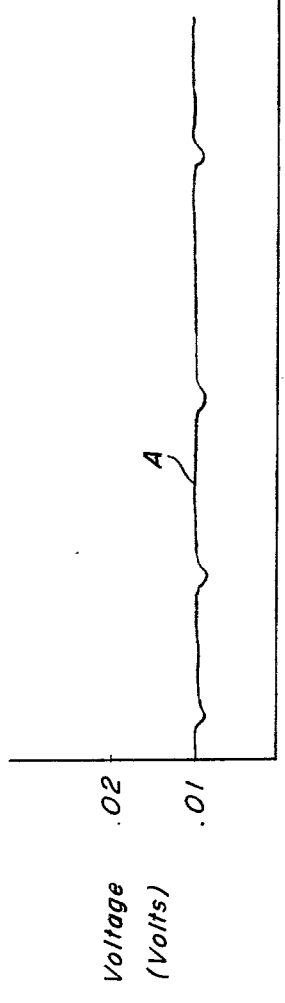
FIGS. 2a, 2b, and 2c are graphical representations of the heart beat signal from an individual, a voltage ramp generated in response to the heartbeat signal, and the interpolated pulse signal, respectively.
Figure 2B:
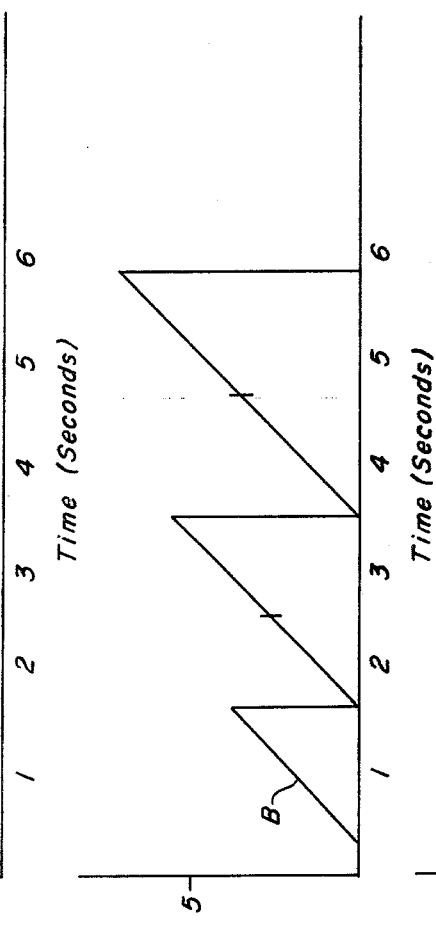
Figure 2C:
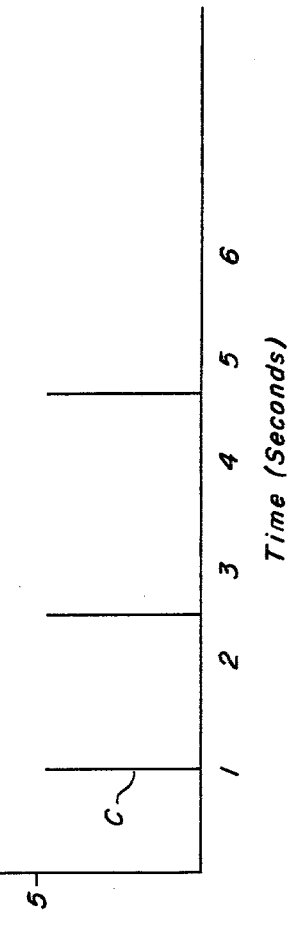

Referring now to FIG. 2, the relationship between the first and second pulse signals and the voltage ramp output is illustrated graphically. FIG. 2a illustrates the heartbeat pulses A of an individual. The voltage ramp B produced by the voltage ramp generator for the sequence of pulses of FIG. 2a is shown in FIG. 2b. Each pulse signal corresponding with a beat of the individual's heart produces a linear voltage ramp which increases until the successive pulse is produced. The voltage ramp generator responds to the next successive heartbeat of the individual, at which time the voltage drops and begins increasing linearly once again. Thus, the leading positive edge of the voltage ramp coincides with the previous heartbeat and the next successive heartbeat resets the voltage ramp generator to produce the next voltage ramp. As shown in FIG. 2b, the amplitude of the voltage ramp peaks varies in accordance with the time between successive heartbeats of the individual. The peak detector and comparator means cooperate to sense a midpoint of each successive voltage ramp. The comparator produces an output pulse which is the second pulse signal for the midpoint of each voltage ramp. The output pulses C of the second pulse signal corresponding with the aforementioned midpoints of the voltage ramps are shown in FIG. 2c. The combination of the pulses shown in FIGS. 2a and 2c results in a sequence of output pulses having a frequency which is twice that of the heartbeat rate of an individual.

The first and second signals corresponding with the heartbeat and the interpolated midpoint signals, respectively, are delivered to a physical stimulus device to produce a pulsed stimulus having a frequency of twice the heartbeat rate of the individual. Referring once again to FIG. 1, the first signal is delivered to one input of a pulse generator 16 via the gate device 18. Similarly, the second signal is delivered to the second input of the pulse generator 16 from the comparator 14. The output from the pulse generator is delivered to an opto-coupler device 20 which activates a lamp 22 in response to the first and second signals applied to the pulse generator device 16. Thus, a visual pulsed stimulus from the lamp 22 is produced in response to the first and second signals, the frequency of the pulsed stimulus being twice the heartbeat rate of the individual. A loudspeaker device 24 is also provided to produce an audio pulse stimulus. The loudspeaker device includes a first input connected with the gate device 18 via a switch 26 and a second input connected with the comparator 14 via a switch 28. By selectively actuating the switches 26 and 28, the pulsed stimulus supplied to the individual may be a total visual stimulus, i.e., when the switches 26 and 28 are opened, or a combination of a pulsed visual and audio stimuli when one of both of the switches 26, 28 are closed. Furthermore, the switches 26, 28 may be ganged if desired.

Figure 3:
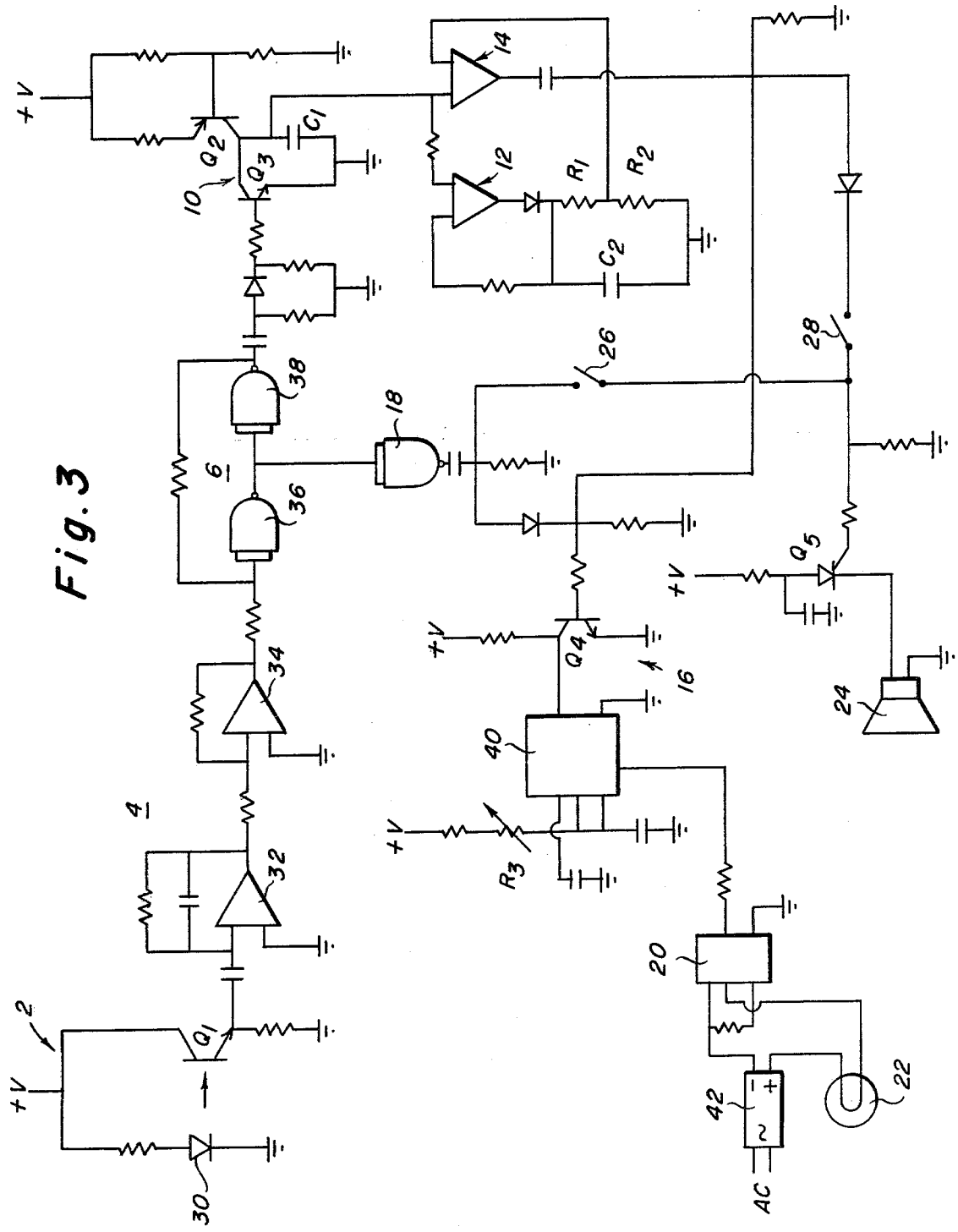
FIG. 3 is a circuit diagram of the device of FIG. 1.

Referring now to FIG. 3, the electrical circuit of the biofeedback device will be described. The heartbeat sensor 2 is adapted for attachment to the finger of an individual to sense the individual's heartbeat rate while minimizing the discomfort to the individual which further aids in inducing a relaxed state. The heartbeat sensor comprises an electro-optical sensor, for example, including an infrared light-emitting diode 30 and a photo-transistor Q1. The light-emitting diode senses changes in the blood concentration in the individual's finger and delivers its output to the base of the photo-transistor Q1 to activate the transistor to produce the first pulse signal which corresponds with the heartbeat rate of the individual. The first signal from the photo-transistor Q1 is applied to the amplifier 4 comprising first and second amplifiers 32 and 34 which amplify the first signal. The amplifiers are used to change the state of a regenerative comparator such as the Schmitt trigger 6 comprising the gates 36 and 38. The Schmitt trigger modifies the amplified first signal to produce a pulsed output having fast pulse transition times suitable for timing the remainder of the operation.

The modified first signal is supplied to the interpolation device to produce the second pulse signal the pulses of which occur midway in time between successive pairs of the first heartbeat pulse signals, respectively. The interpolation device includes the voltage ramp generator 10 comprising the transistor Q2 and capacitor C1. Transistor Q2 is a constant current generator that charges the capacitor C1 to produce a voltage ramp that rises linearly with time as shown in FIG. 2b. The leading positive edge of the signal from gate 38, coinciding with a heartbeat, is applied to transistor Q3 to reset the voltage across the capacitor C1 to zero for the next signal corresponding with the next successive heartbeat. Thus a voltage ramp is generated having voltage peaks in synchronization with the heartbeat, the amplitude of the peaks depending on the heartbeat rate.

The voltage ramp is applied to the peak detector 12 and the peak value is stored in capacitor C2. Resistors R1 and R2 form a voltage divider which biases a comparator 14 to one-half the peak ramp value. When the next succeeding ramp rises past the half peak value representing the time midway between a pair of successive heartbeats, the comparator 14 changes state to provide an electronically interpolated second pulse signal the pulses of which occur midway in time between the aforementioned successive pairs of heartbeat pulses.

The first pulse signal derived directly from the heartbeat of the individual is supplied from the Schmitt trigger 6 to a pulse generator via the gate 18. The pulse generator preferably comprises a transistor Q4 and a conventional multivibrator 40, such as a National type NE555, to provide an output pulse to a stimulator device.

A visual stimulator device includes an opto-coupler 20 connected with the multivibrator 40, and an illumination lamp 22 driven by a full-wave rectifier bridge 42 in response to the pulses from the multivibrator. A variable resistor R3 is provided to control the illumination of the lamp 22. The opto-coupler is of any conventional type such as the Monsanto MCS-2.

The biofeedback device also includes an audio physical stimulus device connected with the gate 18 via the switch 26 and with the comparator 14 of the interpolation device via the switch 28. The audio stimulus device includes a silicon controlled rectifier Q5 which drives a transducer such as the small loudspeaker 24. Selective operation of the switches 26 and 28 controls the physical stimulus produced by the device. Thus, if both switches 26 and 28 are open, only a visual physical stimulus will be produced by the device at a rate of two pulses per heartbeat. If the switch 26 is closed, the visual stimulus will be produced as above and an audio stimulus will be produced at a rate of one pulse per heartbeat, the audio stimuli being synchronized with the heartbeats. If, however, only the switch 28 is closed, the audio stimuli will be produced at a rate of one pulse per heartbeat, the audio stimuli occurring between the heartbeats and being combined with the aforementioned visual atimulus. Finally, if both switches are closed, a combined audio visual stimulus will be produced having a frequency of twice the heartbeat rate of the individual.

While the circuit illustrated in FIG. 3 uses analog techniques to generate the second interpolated pulse signal, the second signal could also be derived by appropriate digital circuitry or by the use of a microcomputer. Furthermore, the first signal could be produced by any suitable sensor means. Thus the transistor Q1 of the electro-optical sensor could be replaced by a photoresistor. Furthermore, the electro-optical sensor could be replaced by any suitable heartbeat sensing device such as a pressure transducer, a sound transducer or an electrocardiogram device.

While the device according to the invention has been described as a means for inducing drowsiness, the biofeedback device is also suitable for regulating an abnormally irregular heartbeat of an individual.

While in accordance with the provisions of the Patent Statutes the preferred forms and embodiments of the invention have been illustrated and described, it will be apparent to those skilled in the art that various changes and modifications may be made without deviating from the inventive concepts set forth above.

What is claimed is:

1. A device for inducing a pre-hypnotic state in an individual, comprising
   (a) means for producing a first pulse signal the pulses of which correspond with the heartbeat of the individual;
   (b) interpolation means connected with said first signal producing means for producing a second pulse signal the pulses of which occur midway in time between successive pairs of said first heartbeat pulses, respectively, said interpolation means including
      (1) voltage ramp generator means responsive to said first pulse signal for producing a linear voltage ramp output the peaks of which are in synchronization with the pulses of said first signal, respectively, the amplitude of said voltage peaks corresponding with the heartbeat rate of the individual;
      (2) peak detector means for sensing the peaks of said voltage ramp output; and
      (3) comparator means connected with said peak detector means for sensing the mid-point of said voltage ramp output between successive peaks, thereby to produce said second signal; and
   (c) stimulus means having a pair of inputs connected with said first signal producing means and with said interpolation means, respectively, for producing a pulsed physical stimulus in response to said first and second signals, said pulsed stimulus having a frequency of twice the heartbeat rate of the individual, whereby a state of profound relaxation is induced when the pulsed stimulus is applied to the individual, and further whereby the individual's mind is receptive to suggestion.

2. Apparatus as defined in claim 1, wherein said first signal producing means comprises
   (1) heartbeat sensor means for sensing the heartbeat of the individual and for producing said first pulse signal;
   (2) amplifier means connected with said heartbeat sensor means for amplifying said first pulse signal; and
   (3) regenerative comparator means connected with said amplifier means for modifying said first pulse signal to produce a fast pulse transition time.

3. Apparatus as defined in claim 2, wherein said heartbeat sensor means comprises an electro-optic sensor.

4. Apparatus as defined in claim 2, wherein said regenerative comparator means comprises a Schmitt trigger.

5. Apparatus as defined in claim 4, wherein said stimulator means comprises visual stimulator means.

6. Apparatus as defined in claim 5, wherein said visual stimulator means includes
   (1) pulse generator means for producing a plurality of pulses in response to said first and second signals;
   (2) opto-coupler means connected with said pulse generator means; and
   (3) lamp means activated by said opto-coupler means in response to said pulses.

7. Apparatus as defined in claim 6, wherein said pulse generator means comprises a transistor which receives said first and second signals, and a multivibrator triggered by said transistor.

8. Apparatus as defined in claim 7, and further including gate means for supplying said first signal to said transistor.

9. Apparatus as defined in claim 8, wherein said stimulator means further comprises audio stimulator means.

10. Apparatus as defined in claim 9, wherein said audio stimulator means includes
    (1) loudspeaker means;
    (2) first switch means for connecting said loudspeaker means with said gate means; and
    (3) second switch means for connecting said loudspeaker with said interpolation means, whereby operation of the first and second switch means controls said loudspeaker relative to the heartbeat of the individual.

11. A method for inducing a pre-hypnotic state in an individual, comprising the steps of
    (a) sensing the heartbeat rate of the individual;
    (b) interpolating the point midway in time between successive pairs of heartbeats of the individual;
    (c) producing a physical pulse stimulus for each heartbeat and each midpoint between successive pairs of heartbeats, respectively, said pulse stimuli being in synchronization with and having a frequency of twice the heartbeat rate of the individual; and
    (d) supplying said pulse stimuli to the individual.

12. A method as defined in claim 11, wherein said pulse stimuli comprise visual signals.

13. A method as defined in claim 11, wherein said pulse stimuli comprise audio signals.

14. A method as defined in claim 11, wherein said pulse stimuli comprise visual and audio signals.

* * * * *